United States Patent
Barsony (10) Patent No.: US 7,361,664 B2
(45) Date of Patent: Apr. 22, 2008

(54) VITAMIN D RECEPTOR ANTAGONISTS AND RELATED COMPOSITIONS AND METHODS OF USE

(75) Inventor: Julianna Barsony, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 410 days.

(21) Appl. No.: 10/481,052

(22) PCT Filed: Jun. 20, 2002

(86) PCT No.: PCT/US02/19774

§ 371 (c)(1),
(2), (4) Date: Mar. 19, 2004

(87) PCT Pub. No.: WO03/000634

PCT Pub. Date: Jan. 3, 2003

(65) Prior Publication Data

US 2004/0152668 A1    Aug. 5, 2004

Related U.S. Application Data (60) Provisional application No. 60/300,409, filed on Jun. 22, 2001, provisional application No. 60/299,570, filed on Jun. 20, 2001.

(51) Int. Cl.
| | |
|---|---|
| C07D 239/70 | (2006.01) |
| C07D 487/12 | (2006.01) |
| C07C 69/74 | (2006.01) |
| C07C 233/05 | (2006.01) |
| A61K 43/48 | (2006.01) |
| A61K 31/22 | (2006.01) |
| A61K 31/16 | (2006.01) |
| A61K 31/165 | (2006.01) |
| A61P 35/04 | (2006.01) |
| A61P 35/02 | (2006.01) |
| A61P 19/08 | (2006.01) |
| A61P 17/06 | (2006.01) |
| A61P 3/02 | (2006.01) |
| A61P 5/18 | (2006.01) |

(52) U.S. Cl. .................. 514/267; 514/546; 514/549; 544/250; 560/126

(58) Field of Classification Search .................. None
See application file for complete search history.

(56) References Cited

U.S. PATENT DOCUMENTS 4,721,727 A * 1/1988 Mikolajczak et al. ....... 514/473
5,830,885 A   11/1998 Posner
6,034,074 A   3/2000 Rodriguez et al.

OTHER PUBLICATIONS

Barsony et. al. (Anal. Biochem., 1995, 229, 68-79.*
Barsony et al., "Development of a Biologically Active Fluorescent-Labeled Calcitriol and Its Use to Study Hormone Binding to the Vitamin D Receptor," *Anal. Biochem.*, vol. 229, pp. 68-79 (1995).

(Continued)

*Primary Examiner*—Brenda Coleman
*Assistant Examiner*—Susanna Moore
(74) *Attorney, Agent, or Firm*—Leydig, Voit & Mayer, Ltd.

(57) ABSTRACT

A compound of formula:

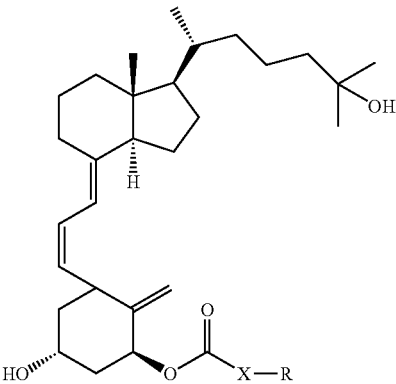

wherein X is a $C_{2-10}$ spacer, and R is a substituted or unsubstituted $C_{6-30}$ aryl, a substituted or unsubstituted $C_{5-30}$ heteroaryl, or

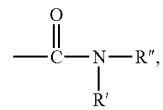

Where R' and R" are independently a substituted or unsubstituted aryl or a substituted or unsubstituted alkyl, wherein said compound is a vitamin D receptor (VDR) antagonist, a compound comprising same, and a method of treating a patient for a disease that can be treated prophylactically or therapeutically by administration of a VDR antagonist, which method comprises administering an effective amount of aforementioned compound or composition, whereupon the patient is treated prophylactically or therapeutically for the disease.

9 Claims, 7 Drawing Sheets

OTHER PUBLICATIONS

Barsony et al., "Differential Regulation of Vitamin D and Glucocorticoid Receptor Targeting by Agonists and Antagonists" (Abstract), *Annual Meeting of the American Society for Bone and Mineral Research*, No. T236, p. S258 (1998).

Barsony et al., "Partial Vitamin D Antagonists Inhibit Breast Cancer Growth In Vitro and In Vivo," *Endo 2001 Denver*, No. OR29-1, pp. 106-107 (2001).

Barsony et al., "Intracellular Trafficking of Glucocorticoid and Vitamin D Receptors is Differentially Regulated by Agonists and Antagonist" (Abstract), *11th International Workshop on Calcified Tissues*, p. 94 (1999).

Bogaerts et al., "Crystallization and Preliminary X-ray Investigation of the Human Vitamin D Binding Protein in Complex with 25-Hydroxyvitamin $D_3$," *Vitamin D Endocrine System: Structural, Biological, Genetic and Clinical Aspects*, vol. 1, pp. 117-120 (2000).

Colston et al., "1,25-Dihydroxyvitamin $D_3$ and Malignant Melanoma: The Presence of Receptors and Inhibition of Cell Growth in Culture," *Endo.*, vol. 108 (3), pp. 1083-1086, (1981).

Dokoh et al., "Influence of 1,25-Dihydroxyvitamin $D_3$ on Cultured Osteogenic Sarcoma Cells: Correlation with the 1,25-Dihydroxyvitamin $D_3$ Receptor," *Cancer Res.*, vol. 44, pp. 2103-2109 (1984).

Eisman et al., "Suppression of in Vivo Growth of Human Cancer Solid Tumor Xenografts by 1,25-Dihydroxyvitamin $D_3$," *Cancer Res.*, vol. 47, pp. 21-25 (1987).

El Abdaimi et al., "The Vitamin D Analogue EB 1089 Prevents Skeletal Metastasis and Prolongs Survival Time in Nude Mice Transplanted with Human Breast Cancer Cells," *Cancer Res.*, vol. 60, pp. 4412-4418 (2000).

Narvaez et al., "Characterization of a Vitamin $D_3$-Resistant MCF-7 Cell Line," *Endo.*, vol. 137 (2), pp. 400-409 (1996).

Ogata, "D Hormone Analogs for Anticancer Treatment," *The Japanese Journal of Clinical Dialysis*, vol. 17 (2), (2001).

Sato et al., "Antitumor Effect of $1\alpha$-Hydroxyvitamin $D_3$," *Tohoku J. Exp. Med.*, vol. 138, pp. 445-446 (1982).

\* cited by examiner

VITAMIN D RECEPTOR ANTAGONISTS AND RELATED COMPOSITIONS AND METHODS OF USE

This application is the U.S. national phase of PCT/US02/19774, which was filed on Jun. 20, 2002, and which claims the benefit of U.S. provisional patent application Nos. 60/299,570, which was filed on Jun. 20, 2001, and 60/300,409, which was filed on Jun. 22, 2001.

FIELD OF THE INVENTION

The present invention relates to vitamin D receptor antagonists, compositions comprising same, and the use of such antagonists or compositions in the treatment of a patient for a disease, such as a disease characterized by abnormal cellular proliferation, e.g., cancer, that can be treated prophylactically or therapeutically by administration of a vitamin D receptor (VDR) antagonist.

BACKGROUND OF THE INVENTION

Vitamin D is a well-known, fat-soluble hormone involved in mineral metabolism and bone growth. It is an essential positive regulator of calcium homeostasis. It can further dramatically facilitate intestinal absorption of calcium, although it also stimulates absorption of phosphate and magnesium ions. In the absence of vitamin D, dietary calcium is not efficiently absorbed at all and this leads to rickets. Increased parathyroid hormone levels are the first indication of rickets-associated vitamin D deficiency.

Vitamin D does not save significant biological activity. Rather, it must be metabolized within the body to the hormonally-active form, calcitriol (1,25-dihydroxycholecalciferol; 1,25-dihydroxy vitamin D3) with the following structure:

This transformation occurs in the liver, where cholecalciferol (vitamin D3) is hydroxylated to 25-hydroxycholecalciferol by the enzyme 25-hydroxylase; and in the kidney, where 25-hydroxycholecalciferol serves as a substrate for 1-α-hydroxylase, yielding 1,25-dihydroxycholecalciferol, i.e., calcitriol, the biologically active form of vitamin D. Calcitriol is a secosteroid that acts through binding to the VDR inside cells. VDRs have been suggested to reside in the cytoplasm and in the nucleus without hormone in an unbound state. The VDR binds several forms of cholecalciferol; however, its affinity for 1,25-dihydroxycholecalciferol is roughly 1,000 times that of 25-hydroxycholecalciferol.

By activating the VDR, calcitriol stimulates the expression of a number of proteins involved in transporting calcium from the lumen of the intestine, across the epithelial cells and into blood. VDRs are present in most, if not all, cells in the body. Additionally, experiments using cultured cells have demonstrated that vitamin D has potent effects on the growth and differentiation of many types of cells. These findings suggest that vitamin D has physiologic effects beyond playing a role in mineral homeostasis and bone function.

Calcitriol, the active hormonal form of vitamin D, also acts through the VDR to regulate important functions, such as cellular proliferation and differentiation and immune functions. Calcitriol has biphasic effects on cell growth, where physiological doses stimulate cell proliferation, and high pharmacological doses inhibit cell growth. Calcitriol and its derivatives are thought to have utility in the treatment of cancers by retarding tumor growth, inducing apoptosis, and stimulating the differentiation of malignant cells. Current calcitriol derivatives are administered in large dosages to inhibit cancer growth. Unfortunately, such large dosages result in toxic levels of serum calcium. Further, the therapeutic possibilities of 1,25-dihydroxycholecalciferol are severely limited by the potent effect of this hormone on calcium metabolism, since serious side effects due to hypercalcemia will result from the high doses necessary to obtain a therapeutic effect on, for example, psoriasis, cancer or immunological disorders. In order to inhibit cell growth, current methodologies utilize combinations of vitamin D derivatives and therapies that specifically alleviate calcemic toxicities incurred by such high pharmacological dosages.

For example, 1,25-dihydroxycholecalciferol possesses potent anti-leukemic activity by inducing the differentiation of leukemia cells. Narvaez et al. (Endo. 137: 400-409 (1996)) disclose studies using EB 1089, which is a vitamin D analogue that induces breast tumor regression. Further, Colston et al. (Endo. 108: 1083-1086 (1981)) report anti-tumor effects of vitamin D derivatives. This study reports the presence of specific, high-affinity receptors for 1,25-dihydroxyvitamin D3 in malignant melanoma, and that in vitro administration of 1,25-dihydroxyvitamin D3 produces a marked increase in cell doubling time. Sato et al. (Tohoku J. Exp. Med. 138: 445-446 (1982)) report the utility of 1α-hydroxyvitamin D3 in in vivo experiments relating to the treatment of Sarcoma 180 and Lewis lung carcinoma implanted into mice. In these experiments, the vitamin D suppressed tumor growth, or inhibited pulmonary metastases. In another study, Disman et al. (Canc. Res. 47: 21-25 (1987)) disclose the utility of 1,25-dihydroxyvitamin D3 for inhibiting the growth of human colonic cancer xenografts in mice. Furthermore, Dokoh et al. (Canc. Res. 44: 2103-2109 (1984)) disclose the utility of 1,25-dihydroxyvitamin D3 on cultured osteogenic sarcoma cells.

Vitamin D and its analogues, while potentially useful in retarding abnormal cellular proliferation or tumor growth, have the disadvantage of being potent calcemic agents that cause elevated blood calcium levels by stimulating intestinal calcium absorption and bone calcium resorption. Accordingly, there has been a desire in the art for vitamin D analogues and derivatives having variant activities such that, for example, anti-leukemic activity is enhanced without concomitant enhancement of calcemic activity or toxicity. The present invention provides such analogues and derivatives. This and other objects and advantages, as well as additional inventive features, will be apparent from the detailed description provided herein.

BRIEF SUMMARY OF THE INVENTION

The present invention provides a compound of formula:

wherein X is a $C_{2-10}$ spacer, and R is a substituted or unsubstituted $C_{6-30}$ aryl, a substituted or unsubstituted $C_{5-30}$ heteroaryl, or where R' and R" are independently a substituted or unsubstituted aryl or a substituted or unsubstituted alkyl, wherein the compound is a VCR antagonist, with a proviso that, when X is CH2CH2, R is not 4,4-difluoro-5,7-dimethyl-4-bora-3a,4a-diaza-s-indacene. The present invention further provides a composition comprising such a compound and carrier therefor. Still further provided is a method of treating a patient for a disease that can be treated prophylactically or therapeutically by administration of a VDR antagonist. The method comprises administering an effective amount of a compound of formula:

wherein X is a $C_{2-10}$ spacer, and R is a substituted or unsubstituted $C_{6-30}$ aryl, a substituted or unsubstituted $C_{5-30}$ heteroaryl, or where R' and R" are independently a substituted or unsubstituted aryl or a substituted or unsubstituted alkyl, wherein the compound is a VDR antagonist, whereupon the patient is treated prophylactically or therapeutically for the disease.

DETAILED DESCRIPTION OF THE INVENTION

The present invention provides novel VDR modulators, antagonists, or inhibitors (referred to herein generically as VDR antagonists). More specifically, the present invention provides a modified calcitriol, which has been modified at position 1 of the A ring. Previous attempts to modify position 1 of the A-ring severely impaired the ability of the compound to bind to the VDR. This problem was solved by adding an ester bond and a spacer.

The VDR antagonists provided herein have been demonstrated to bind to VDRs with high affinity. Further, the antagonists compete with calcitriol for binding to the receptor, to regulate gene transcription and cell growth. These compounds can negatively regulate the ability of the VDR to stimulate cell proliferation. These antagonists can be used for the treatment of abnormal cell growth, such as cancer, and the prevention of recurrent cancers. One preferred embodiment of the invention utilizes the VDR antagonists for the therapeutic treatment of breast cancer and prophylactic treatment of recurrent breast cancer. The VDR antagonists of the invention can also be used for the therapeutic treatment and/or prophylactic prevention of other types of conditions or diseases, such as, but not limited to, prostate cancer, colorectal cancer, leukemia, brain cancer, primary or metastatic melanoma, glioma, primary hyperparathyroidism, psoriasis, and kidney stones. Furthermore, since these derivatives inhibit parathyroid hormone secretion, they are contemplated to be effective for the treatment of secondary hyperparathyroidism that causes bone disease and vascular calcification in patients suffering from renal failure.

The compounds of the present invention embrace calcitriol that has been modified at position 1 (alone or in further combination with position 3) of the A-ring of calcitriol, where a spacer of varying carbon length and a substituted or unsubstituted aryl or heteroaryl or OCNR'R" is attached by an ester bond to calcitriol. Accordingly, the present invention provides a compound or formula:

wherein X is a $C_{2-10}$ spacer, and R is a substituted or unsubstituted $C_{6-30}$ aryl, a substituted or unsubstituted $C_{5-30}$ heteroaryl, or where R' and R" are independently a substituted or unsubstituted aryl, such as a substituted or unsubstituted $C_{6-30}$ aryl, or a substituted or unsubstituted alkyl, such as a substituted or unsubstituted $C_{1-4}$ alkyl, wherein the compound is a VDR antagonist, with the proviso that R is not 4,4-difluoro-5,7-dimethyl-4-bora-3a,4a-diaza-s-indacene when X is $CH_2CH_2$ (BCA11). The compound can have, but need not have, at least one nitrogen, sulfur and/or fluorine atom.

In one embodiment (BCA21), X is $CH_2CH_2$ and substituted or unsubstituted R is 4,4-difluoro-5-styryl-4-bora-3a,4a-diaza-s-indacene, represented structurally as:

In another embodiment, X is $CH_2CH_2$ and R is:

In yet another embodiment, X is $(CH_2)_{10}$ and R is:

In yet another embodiment, X is $CH_2CH_2$ and R is:

In still yet another embodiment, X is $CH_2CH_2$ and R is 4,4-difluoro-5-(2-pyrrolyl)-4-bora-3a,4a-diaza-s-indacene, represented structurally as:

The "spacer" comprises from 2 to 10 carbon atoms. Preferably, the spacer comprises a backbone of at least 2 carbon atoms.

Any suitable "aryl" can be used for R. The term "aryl" refers to an aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 6 to about 30 carbon atoms, preferably from about 6 to about 20 carbon atoms, more preferably from about 6 to about 18 carbon atoms, even more preferably from about 6 to about 14 carbon atoms and most preferably from about 6 to about 10 carbon atoms. It is understood that the term aryl applies to cyclic substituents that are planar and comprise 4n+2 p electrons, according to Hüickel's Rule. The aryl can be unsubstituted or substituted with, for example, substituents described herein.

Any suitable "heteroaryl" also can be used for R. The term "heteroaryl" refers to an aromatic heterocyclic ring, as is commonly understood in the art, including monocyclic and polycyclic heteroaryls containing from, for example, about 5 to about 30 carbon atoms, preferably from about 5 to about 10 carbon atoms, more preferably from about 5 to about 6 carbon atoms. One or more, preferably 1 to 3, carbon atoms are substituted with a heteroatom, such as N, O, or S, to form the heteroaryl moiety. Monocyclic heleroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl. The heteroaryl can be unsubstituted or substituted with, for example, substituents described herein.

The term "alkyl" means a straight-chain or branched alkyl substituent containing from, for example, about 1 to about 12 carbon atoms, preferably from about 1 to about 8 carbon atoms, more preferably from about 1 to about 6 carbon atoms, most preferably from about 1 to about 4 carbon atoms. Examples of such substituents include methyl, ethyl, propyl, isopropyl, n-butyl, sec-butyl, isobutyl, tert-butyl, pentyl, isoarnyl, hexyl, octyl, dodecanyl, and the like. The alkyl can be substituted or unsubstituted with, for example, substituents described herein.

Substituents, which can be used to substitute the above compounds, such as by substitution of an aryl, a heteroaryl, or an alkyl, for example, as described herein, include, but are not limited to, hydroxy, $C_{1-12}$ alkyl, $C_{2-12}$ alkenyl, $C_{2-12}$ alkynyl, $C_{1-12}$ alkoxy, $C_{6-30}$ aryloxy, $C_{1-12}$ benzyloxyalkyl, acyloxy, halo, benzyl, acetyl, carboxyl, carboxy-$C_{1-12}$ alkyl, such as carboxymethyl and carboxyethyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, thiocyano, isothiocyano, tolyl, xylyl, mesityl, anisyl, formyl, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl, $C_{1-12}$ trialkylsilyl, nitro, sulfonyl, nitrobenzyl, $C_{1-12}$ trialkylammonium, $C_{3-8}$ cycloalkyl, $C_{3-8}$ heterocycloalkyl, and OCNR'R", wherein R' and R" are independently, for example, an alkyl, nitrogen, an alkoxy, hydroxy, or amino.

The above compounds can be synthesized in accordance with methods known in the art. See, e.g., Barsony et al., Analytical Biochemistry 229: 68-79 (1995)). See, also, Example 9.

In view of the foregoing, the present invention further provides a composition comprising an above-described compound and a carrier therefor. Preferably, the composition is a pharmaceutical composition and the carrier is pharmaceutically acceptable. Desirably, the composition comprises an above-described compound in an amount effective to modulate, antagonize or inhibit a VDR. Alternatively, a pharmaceutical composition can comprise a pharmaceutically acceptable carrier and a compound of the above general formula (on the left on page 6) in which X is $CH_2CH_2$ and R is 4,4-difluoro-5,7-dimethyl-4-bora-3a,4a-diaza-s-indacene. Such a compound is otherwise known as BCA11. If the composition comprises BCA11, desirably the BCA11 is present in an amount effective to modulate, antagonize or inhibit VDR, i.e., a low dosage, inasmuch as BCA11 at high dosages is known to be a weak agonist of VDR.

Compositions, such as pharmaceutical compositions, comprising an effective amount of the VDR antagonist described above, with a carrier, such as a pharmaceutically acceptable carrier, can be in the form of tablets, capsules, powders, granules, lozenges, suppositories, reconstitutable powders, or liquid preparations, such as oral or sterile parenteral solutions or suspensions. However, for consistency of administration, it is preferred that the composition be in the form of a unit dose. For oral administration, tablets and capsules can contain conventional excipients, such as binding agents, tabletting lubricants, or pharmaceutically acceptable wetting agents, such as sodium lauryl sulphate.

Solid oral compositions can be prepared by conventional methods of blending, filling, tabletting or the like. Repeated blending operations can be used to distribute the VDR antagonist, alone or in further combination with another active agent, throughout any compositions employing fillers. Such operations are, of course, conventional in the art. See, for example, Remington's Pharmaceutical Sciences, 17th Edition, 1985, Gennaro, ed., Mack Pub. Co., PA, USA. The tablets can be coated according to methods well-known in normal pharmaceutical practice, in particular with enteric coating. Oral liquid preparations can be in the form of, for example, emulsions, syrups, or elixirs, or can be presented as a frozen product for reconstitution with water or other suitable vehicle before use. Such liquid preparations can contain conventional additives, such as suspending agents, emulsifying agents, non-aqueous vehicles (which may include edible oils), and, if desired, conventional flavoring or coloring agents.

For parenteral administration, fluid unit dosage forms are prepared utilizing the VDR antagonist and a sterile vehicle, and, depending on the concentration used, either can be suspended or dissolved in the vehicle. In preparing solutions, the VDR antagonist can be dissolved in water for injection and filter-sterilized before filling into a suitable vial or ampoule and sealing. Also, adjuvants, such as local anaesthetic, a preservative, and buffering agents can be dissolved in the vehicle. To enhance stability, the composition can be frozen after filling into the vial and the water removed under vacuum. Parenteral suspensions are prepared in substantially the same manner, except that the VDR antagonist is suspended in the sterile vehicle. A surfactant or wetting agent can be included in the composition to facilitate uniform distribution of the VDR antagonist.

Topical administration can be preferred in certain instances. For example, topical administration can be used to in the treatment of psoriasis and melanoma. Suitable formulations comprising the VDR antagonist described herein can be prepared in accordance with methods known in the art.

In view of the foregoing, the present invention further provides a method of treating a patient for a disease that can be treated prophylactically or therapeutically by administration of a VDR antagonist. Preferably, the VDR antagonist is administered to a patient which maintains serum calcium, phosphorus, liver and renal functions within normal physiological ranges, indicating low toxicity.

By "prophylactically" is meant the inhibition of the onset of the disease to some degree or the absolute prevention of the onset (or recurrence) of the disease. One of ordinary skill in the art readily appreciates that, while absolute prevention of the onset (or recurrence) of disease is desirable, any degree in the inhibition of the onset (or recurrence) of disease can be beneficial. By "therapeutically" is meant the amelioration of the signs and/or symptoms of disease or the curing of disease, One of ordinary skill in the art readily appreciates that, while the cure of disease is desirable, any amelioration of disease can be beneficial.

Any suitable VDR antagonist can be used in the context of the present inventive method. Desirably, the VDR antagonist binds VDR and exerts a prophylactic or therapeutic effect against a disease in a patient, such as by inhibiting abnormal cellular proliferation (such as by inhibiting transcriptional activity and counteracting the growth stimulatory effect of calcitriol), without disrupting bone-protecting properties and/or incurring calcemic toxicities. In this regard, suitable VDR antagonists can be synthesized, such as in accordance with the method of Barsony et al. (1995), supra, and Example 9 and assayed for VDR antagonistic activity in accordance with methods known in the art as well as those set forth herein in the Examples.

Preferably, the method comprises administering an effective amount of a compound of formula:

or wherein X is a $C_{2-10}$ spacer, and R is a substituted or unsubstituted $C_{6-30}$ aryl, a substituted or unsubstituted $C_{5-30}$ heteroaryl, or where R' and R" are independently a substituted or unsubstituted aryl or a substituted or unsubstituted alkyl, wherein the compound is a VDR antagonist, whereupon the patient is treated prophylactically or therapeutically for the disease. The compound can contain, but need not contain, a nitrogen, sulfur or fluorine atom. Aryl, heteroaryl, alkyl, substituents, and spacers are as described above.

Preferably, the disease is characterized by abnormal cellular proliferation, such as cancer, in particular cancer of the breast (including recurrent breast cancer and estrogen-resistant breast cancer), prostate, colon, rectum, or brain. Alternatively, the cancer is leukemia, primary or metastatic melanoma, or glioma. The disease can be primary or secondary hyperparathyroidism, disease of the bone, vascular calcification, renal failure, kidney stones, or psoriasis. Secondary hyperparathyroidism causes bone disease and vascular calcification in patients suffering from renal failure.

The VDR antagonist or a pharmaceutical composition comprising a VDR antagonist can be administered via one of several routes, including intravenous, intramuscular, subcutaneous, intradermal, intraperitoneal, intrathoracic, intrapleural, intrauterine, topical, rectal, vaginal, or intratumoral. Administration also can be by transmucosal or transdermal means. For transmucosal or transdermal administration penetrants appropriate to the barrier to be permeated are used in the formulation. Such penetrants are generally known in the art, and include, for example, for transmucosal administration bile salts and fusidic acid derivatives. In addition, detergents and/or lipids can be used to facilitate permeation. Transmucosal administration can be by nasal sprays, for example, or suppositories. For oral administration, the VDR antagonists or pharmaceutical compositions comprising the like, are formulated into conventional oral administration forms, such as capsules, tablets, and the like. Those skilled in the art will recognize that the mode of administering the VDR antagonist depends on the disease to be treated and that one route of administration may provide a more immediate effect than another route of administration. For example, a preferred mode of administering the VDR antagonist for the treatment of leukemia would involve intravenous administration, whereas preferred methods for treating skin cancer or psoriasis would involve, for example, topical or intradermal administration.

The preferred dosage of the VDR antagonist or pharmaceutical composition thereof, is selected based on other criteria, including the particular composition employed and the age, weight, and condition of the individual. Importantly, the quantity of VDR antagonist used should be sufficient to treat the disease prophylactically or therapeutically, e.g., inhibit cellular proliferation of tumor cells while allowing normnal cells to remain substantially unharmed. In general, it is desirable to provide the patient with a dosage of VDR antagonist to reach steady-state blood concentrations of at least about 0.1 nM, preferably at least about 1 nM, more preferably at least about 4 nM, while a range of from about 0.01 nM to about 1 mM is contemplated, of course, a lower or higher dose may be administered, as determined appropriate by a clinician. As stated above, a variety of clinical factors will influence the preferred dosage ranges.

The pharmaceutical compositions of the invention may contain from 0.1% to 99% by weight, preferably from 10% to 25% by weight of the VDR antagonist, depending on the method of administration.

Combination therapies are also contemplated. For example, if the disease to be treated is cancer, an anti-cancer agent can be co-administered by the same or a different route as the VDR antagonist and simultaneously or sequentially, in either order. In this regard the VDR antagonists of the present invention can be co-administered with an agent that targets the estrogen receptor. Other therapeutic agents that can be co-administered with a VDR antagonist to treat breast cancer include, for example, vitamin D analogues, such as Zemplar (Abbott Laboratories); or estrogen analogues, such as Tamoxifen. Many such reagents and therapeutics are commonly known in the art and can be used in combination with the VDR antagonists described herein.

One of the most important advantages of the VDR antagonists as anti-proliferative agents is their specificity. These selective VDR antagonists counteract the growth stimulatory effect of calcitriol without inhibiting bone-protective effects.' In a further embodiment, the VDR antagonists of the present invention selectively inhibit growth stimulatory effects of calcitriol without causing either hyper- or hypocalcemia or other calcemic toxicities.

The VDR antagonists of the invention can be reversible or irreversible. In vitro studies have demonstrated that the binding of antagonist is reversible. Without being bound by theory, since the VDR antagonist binds its receptor with high affinity, the breakdown is slow, and, therefore, the effect could persist for several weeks. The high affinity binding of VDR antagonists to VDRs inhibits calcitriol's ability to bind to the receptor, regulate gene transcription, and stimulate cell proliferation. As a result, the growth rate of breast cancer cells treated with low concentrations of BCA 11 was 50% of the growth rate of untreated cells.

EXAMPLES

The following examples serve to illustrate the present invention and are not intended to limit its scope in any way.

Example 1

Luciferase Assay

Figure 1:
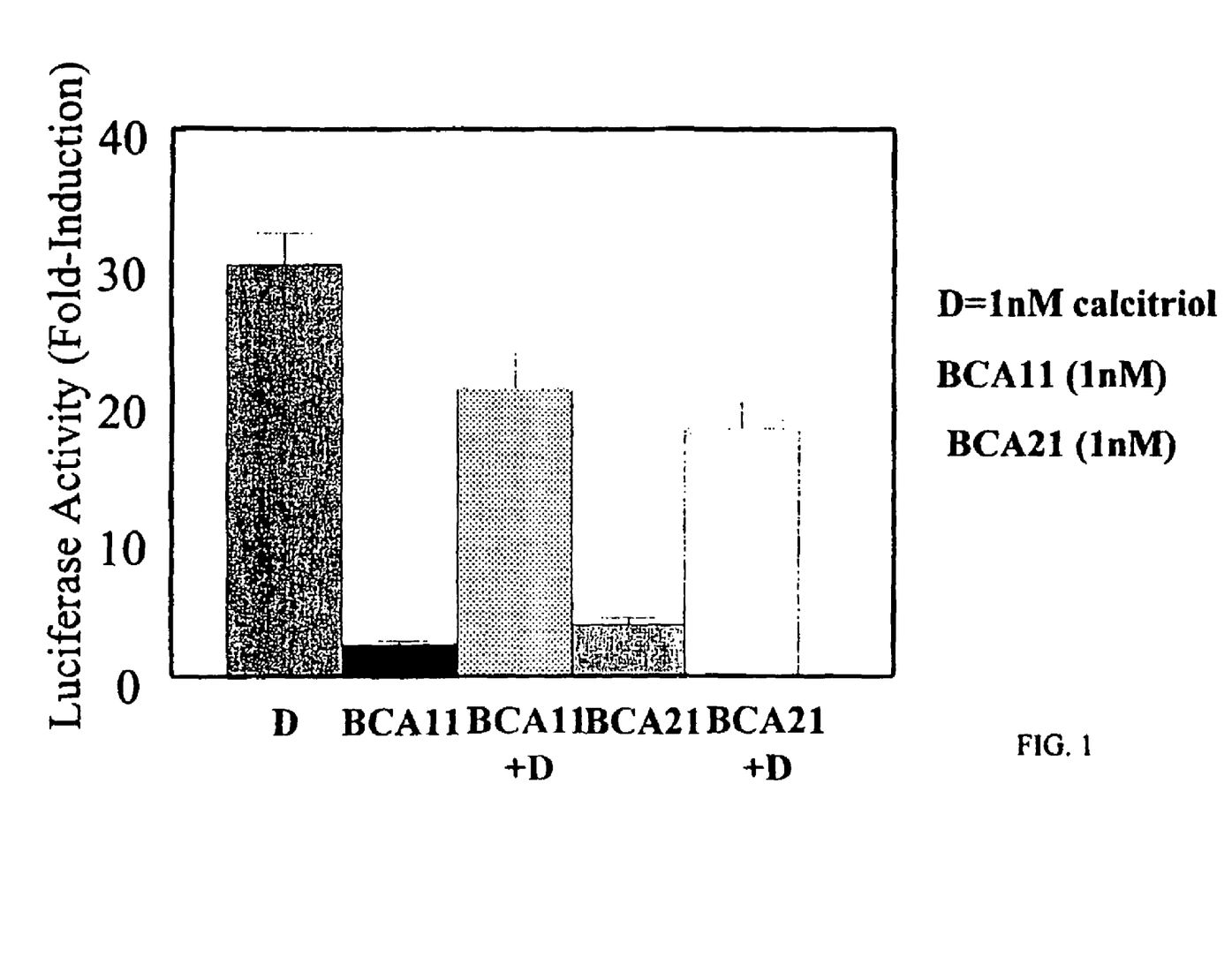
FIG. 1 is a bar graph of luciferase activity (fold-induction) vs. active agent, which shows the inhibition of calcitriol-induced luciferase activity by BCA11 (1 nM), in the presence and absence of calcitriol (1 nM), and BCA21 (1 nM), in the presence and absence of calcitriol (1 nM), as compared to calcitriol (1 nM) alone.

ROS AI cells stably express a luciferase reporter, which is driven by the calcitriol-responsive 24-hydroxylase promoter. These cells were subcultured into 12-well plates and then exposed for 24 h to hormones or vehicle (0.1% ethanol). Luciferase activities were measured with reagents from Promega according to manufacturer's instructions. Activities from hormone-treated cells were compared to activities from vehicle-treated cells (fold-induction). FIG. 1 shows that the addition of BCA11 or BCA21 decreases the ability of calcitriol to stimulate luciferase activity. In MCF-7 cell extracts, 1 nM BCA11 acted as a weak agonist to increase 24-hydroxylase activity, while lower doses antagonized the effect of calcitriol. Table 1 further shows the additive effects of calcitriol and BCA11 in terms of cell growth inhibition.

TABLE 1

| HORMONE | [$^3$H]-Thymidine Incorporation MCF-7 cells (% of Control) |
|---|---|
| Calcitriol (10 nM) | 67 ± 8 |
| BCA11 (10 nM) | 51 ± 9 |
| Calcitriol (10 nM) + BCA11 (10 nM) | 34 ± 6 |

Example 2

[$^3$H]-Thymidine Incorporation Assay

Figure 2:
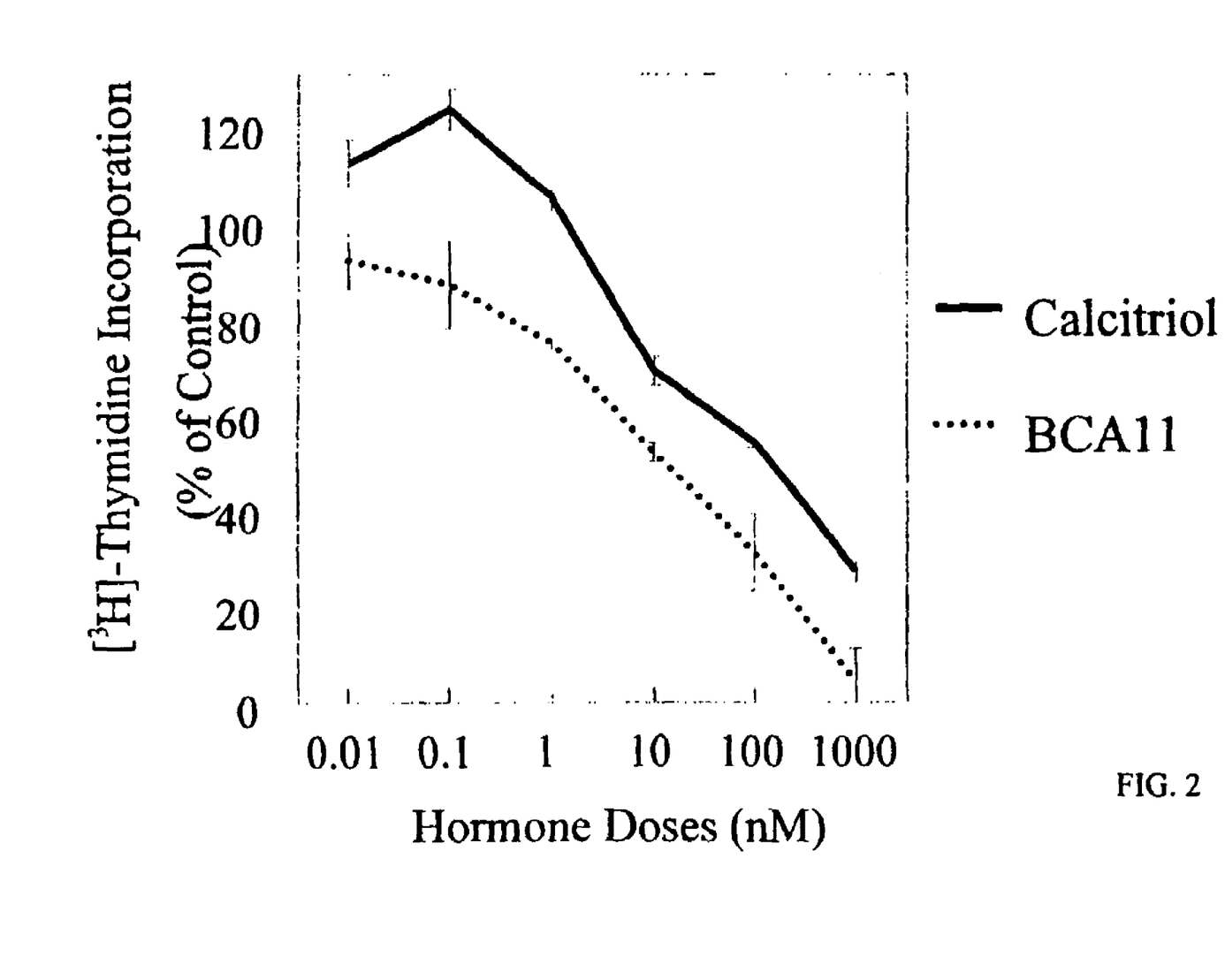
FIG. 2 is a line graph of [$^3$H]-thymidine incorporation (% of control) vs. hormone doses (nM), which shows BCA11 inhibition of [3H]-thymidine incorporation in MCF-7 human breast cancer cells at increasing dosages as compared to calcitriol.

MCF-7 cells (10,000 cells/well) were subcultured in 24 well plates and treated with hormone for 3 days in graded concentrations (FIG. 2). For the last 12 hours, [$^3$H]-thymidine (0.5 µCi/well) was added to cells. Cells were treated with TCA (20% for 15 minutes, twice with 10% for 3 minutes, and ethanol for 3 minutes). Acid-insoluble material was dissolved in 1 N NaOH, then neutralized with 1 N HCl. Radioactivity was measured by liquid scintillation counting. Data were expressed as radioactivity (% of control). The control was cells treated with vehicle (0.1% ethanol). BCA11 inhibited human breast cancer cell proliferation as a measure of incorporated [$^3$H]-thymidine. Anti-proliferative effects of BCA11 and calcitriol were additive. BCA11 was 100 times more effective than calcitriol in inhibiting [$^3$H]-thymidine incorporation in both estrogen-receptor positive (MCF-7, BR3, and T47D) and negative (BT20) breast cancer cells.

Figure 3:
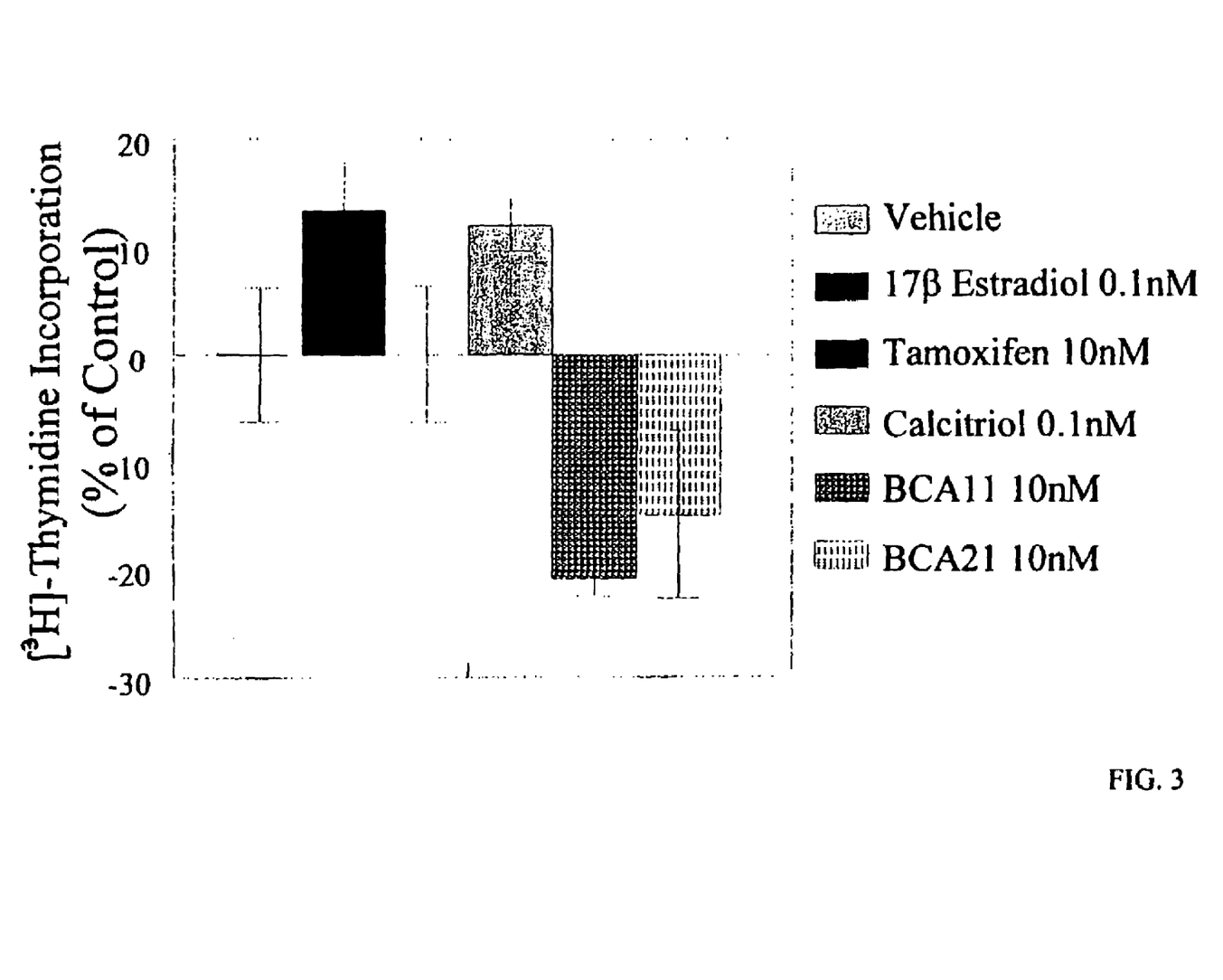
FIG. 3 is a bar graph of [$^3$H]-tymidine incorporation (% of control) vs. active agent, which shows the effect of 17β estradiol, tamoxifen, calcitriol, BCA11, and BCA21 on [$^3$H]-thymidine incorporation in MCF-7 human breast cancer cells as compared to vehicle alone.

FIG. 3 shows the hormonal effects on MCF-7 human breast cancer cell growth. As demonstrated, BCA11 and BCA21 inhibit cell proliferation, whereas the natural form of estrogen, 17β Estradiol, and calcitriol stimulate cell growth.

Example 3

In Vivo Inhibition of Early Stage Tumor Growth

Figure 4A:
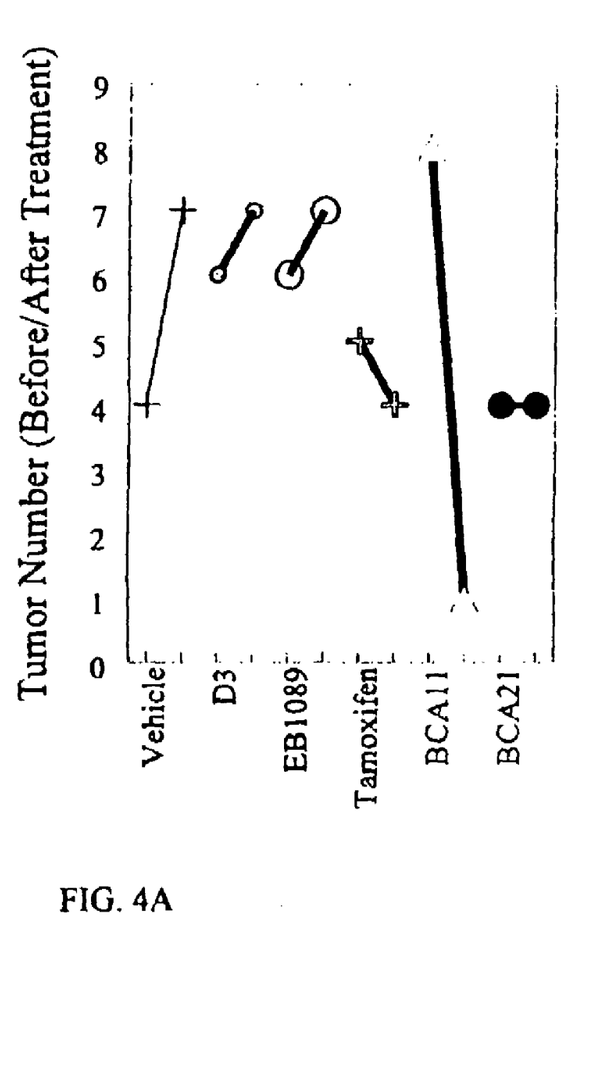
FIG. 4A is a graph of tumor number (before/after treatment) vs. active agent, which shows the effect of vitamin D3, EB1089, tamoxifen, BCA11, and BCA21 on early stage (phase I) breast tumor growth in vivo over a course of five weeks of treatment on alternate days as compared to vehicle alone (control).
Figure 4B:
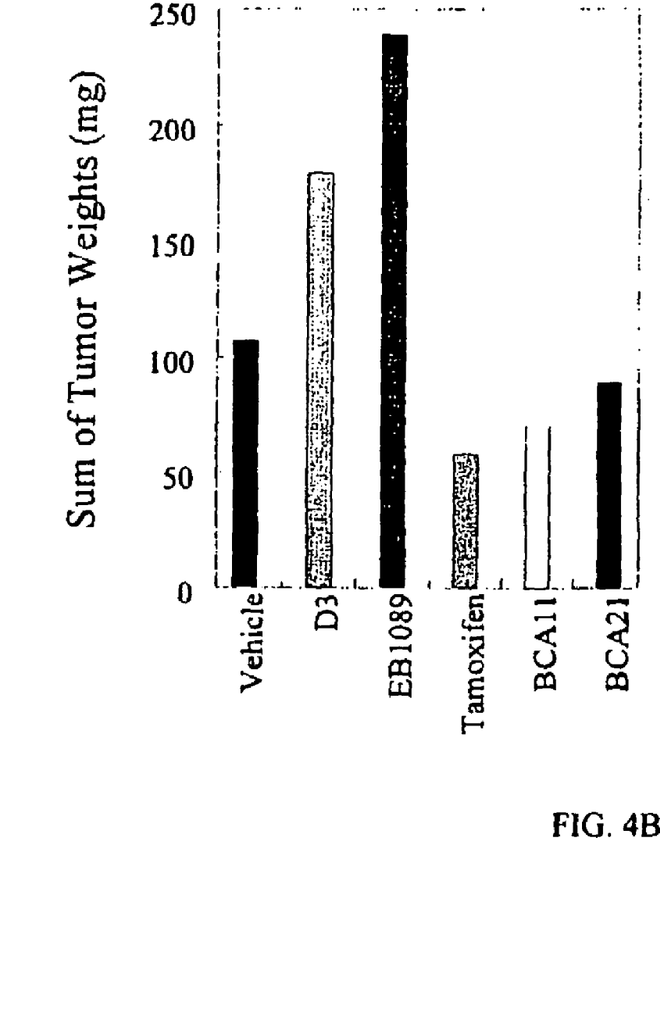
FIG. 4B is a graph of sum of tumor weights (mg) vs. active agent, which shows the effect of vitamin D3, EB1089, tamoxifen, BCA11 and BCA21 on early stage (phase I) breast tumor growth in vivo over a course of five weeks of treatment on alternate days as compared to vehicle alone (control).

MCF-7 cells were injected into 7 weeks old female athymic nude mice (10 mice/treatment group). After four weeks, measurable tumors had developed in each group. Mice were then treated for 5 weeks with hormones or vehicle (propylene glycol) 3 times a week. All of the hormones were added at a concentration of 1 µg/kg, except for Tamoxifen, which was added at a concentration of 2 mg/kg. FIG. 4A shows the tumor number prior to treatment and after treatment with hormone. FIG. 4B shows the sum of tumor weights (mg) that was measured at the end of treatment. The results indicate that BCA11 inhibits tumor growth as well as Tamoxifen and BCA21 also inhibits tumor growth.

Example 4

In Vivo Inhibition of Advanced Stage Tumor Growth

Figure 5:
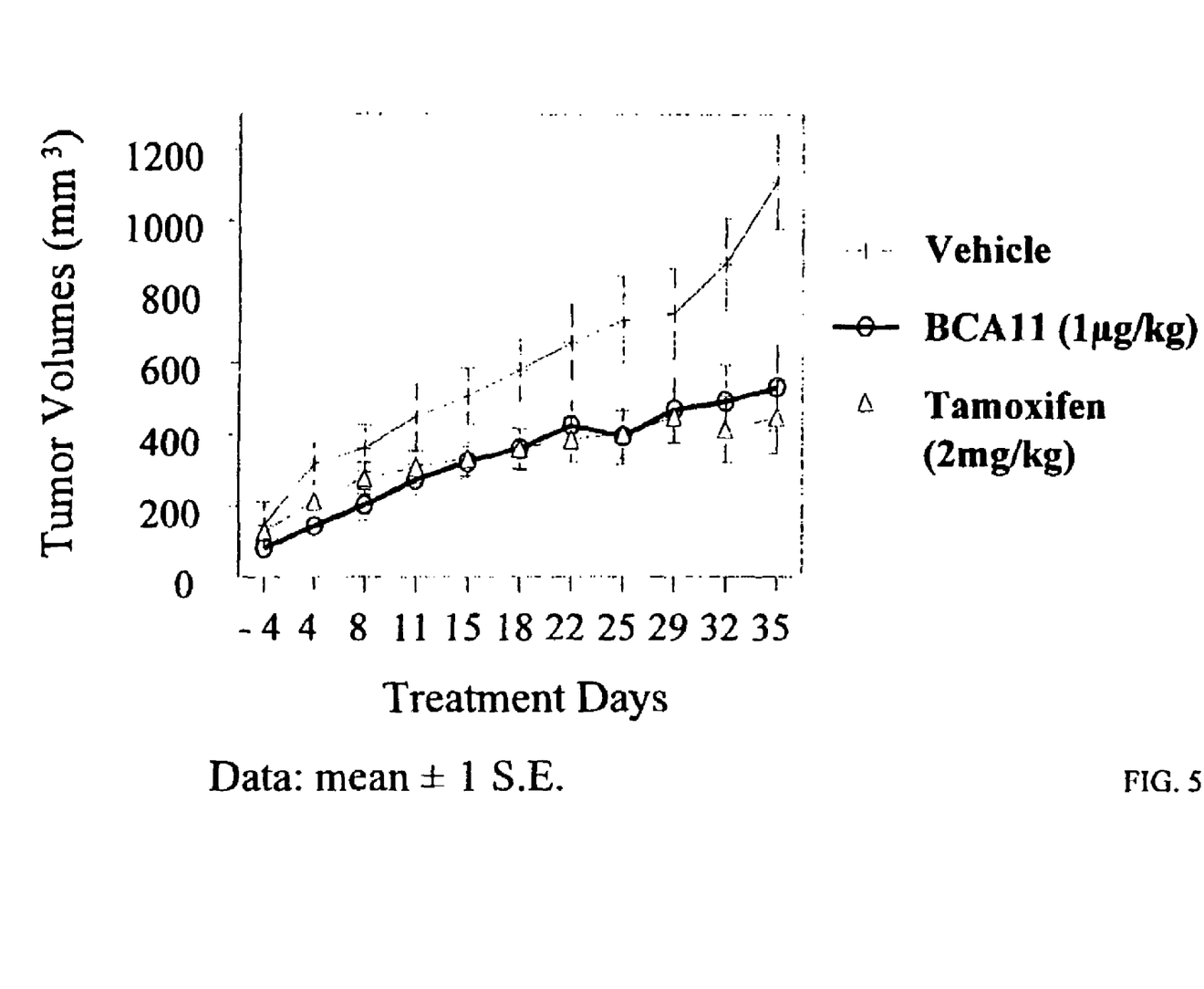
FIG. 5 is a line graph of tumor volume (mm$^3$) vs. treatment day, which shows the effect of treatment with BCA11 or tamoxifen on late or advanced stage (phase II) breast tumor growth in vivo, where tumors were grown in the presence of estrogen (0.72 mg pellets), as compared to vehicle alone (control).

MCF-7 cells were injected with Matrigel (10 mg/ml) into 7 weeks old female athymic nude mice (10 mice/treatment group). Tumors were grown in the presence of implanted estrogen pellets (0.72 mg pellets). Four weeks after inoculation, mice were treated for 5 weeks with hormones or vehicle (propylene glycol) on alternate days. BCA11 was added at a concentration of 1 µg/kg and Tamoxifen was added at a concentration of 2 mg/kg. FIG. 5 shows the tumor volumes ($mm^3$) of late-stage breast cancer in vivo with BCA11 or Tamoxifen treatment over a continuous treatment period. The results indicate that the VDR antagonist, BCA11, is as effective as Tamoxifen in the treatment of advanced stage breast cancer. The tumor volumes as measured on day 35 indicate that either BCA11 or Tamoxifen treatment inhibit tumor growth by about 50% as compared to the control (vehicle alone).

Example 5

In Vivo Suppression of Parathyroid Hormone Levels

Figure 6:
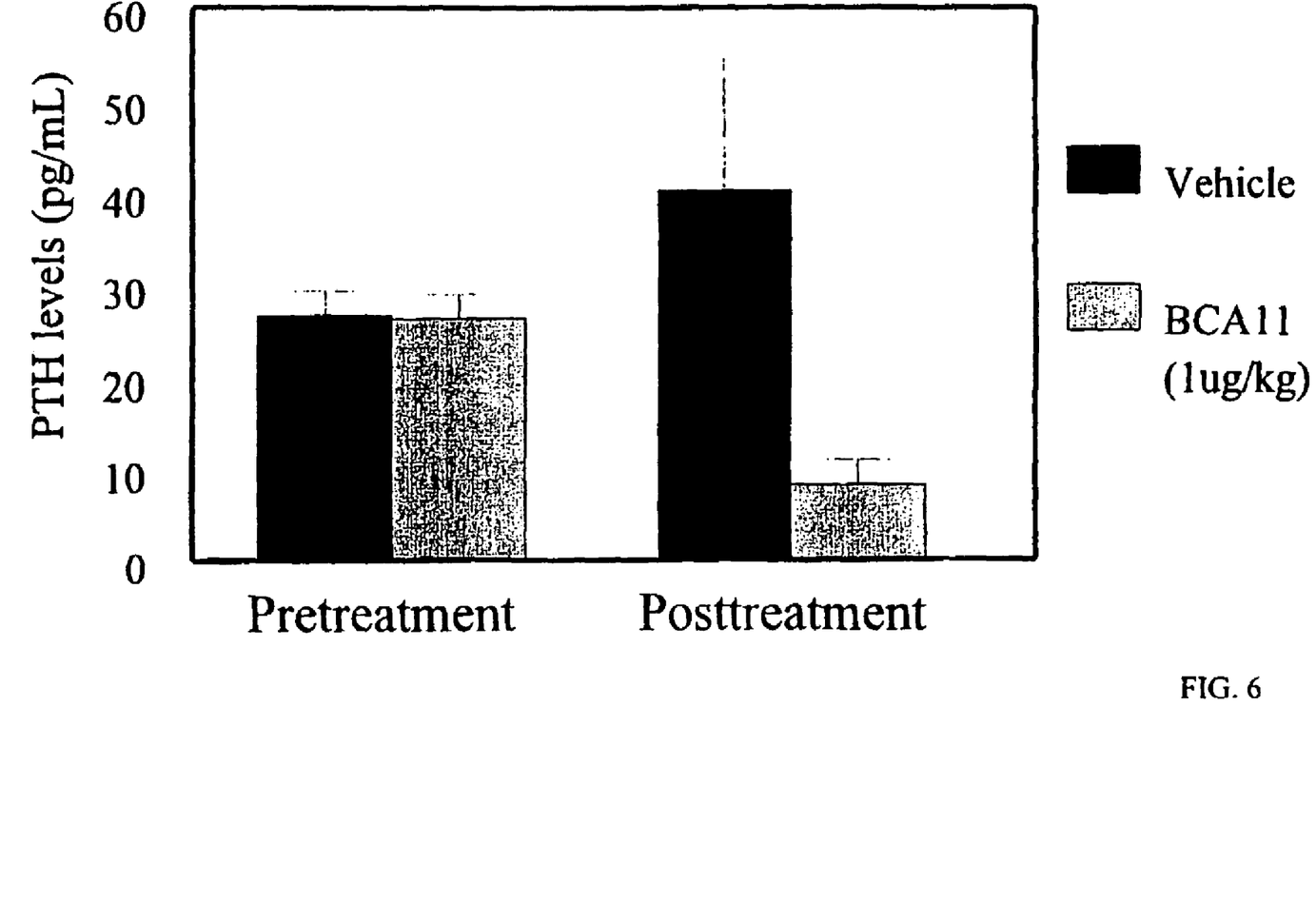
FIG. 6 is a bar graph of parathyroid hormone (PTH) levels (pg/mL) vs. pretreatment and posttreatment with BCA11, which shows the suppression of PTH levels in animals treated with BCA11 as compared to vehicle alone (control).

MCF-7 cells were injected with Matrigel (10 mg/ml) into 7 weeks old female athymic nude mice. Tumors were grown in the presence of implanted estrogen pellets (0.72 mg pellets). After four weeks inoculation, mice were treated for 5 weeks with hormones or vehicle (propylene glycol) on alternate days. BCA11 was added at a concentration of 1 µg/kg. During treatment, mice were maintained on a vitamin D deficient diet. Serum was drawn before and after hormone treatment from the orbital vein of the mice and assayed by Ani Lytics, Inc., by methods well-known in the art. FIG. 6 shows that after BCA11 treatment, parathyroid hormone (PTH) levels as measured by pg/mL decreased significantly as compared to vehicle control or pretreatment levels.

Example 6

Normal Serum Calcium Levels with Chronic in Vivo Administration of BCAL11

Figure 7:
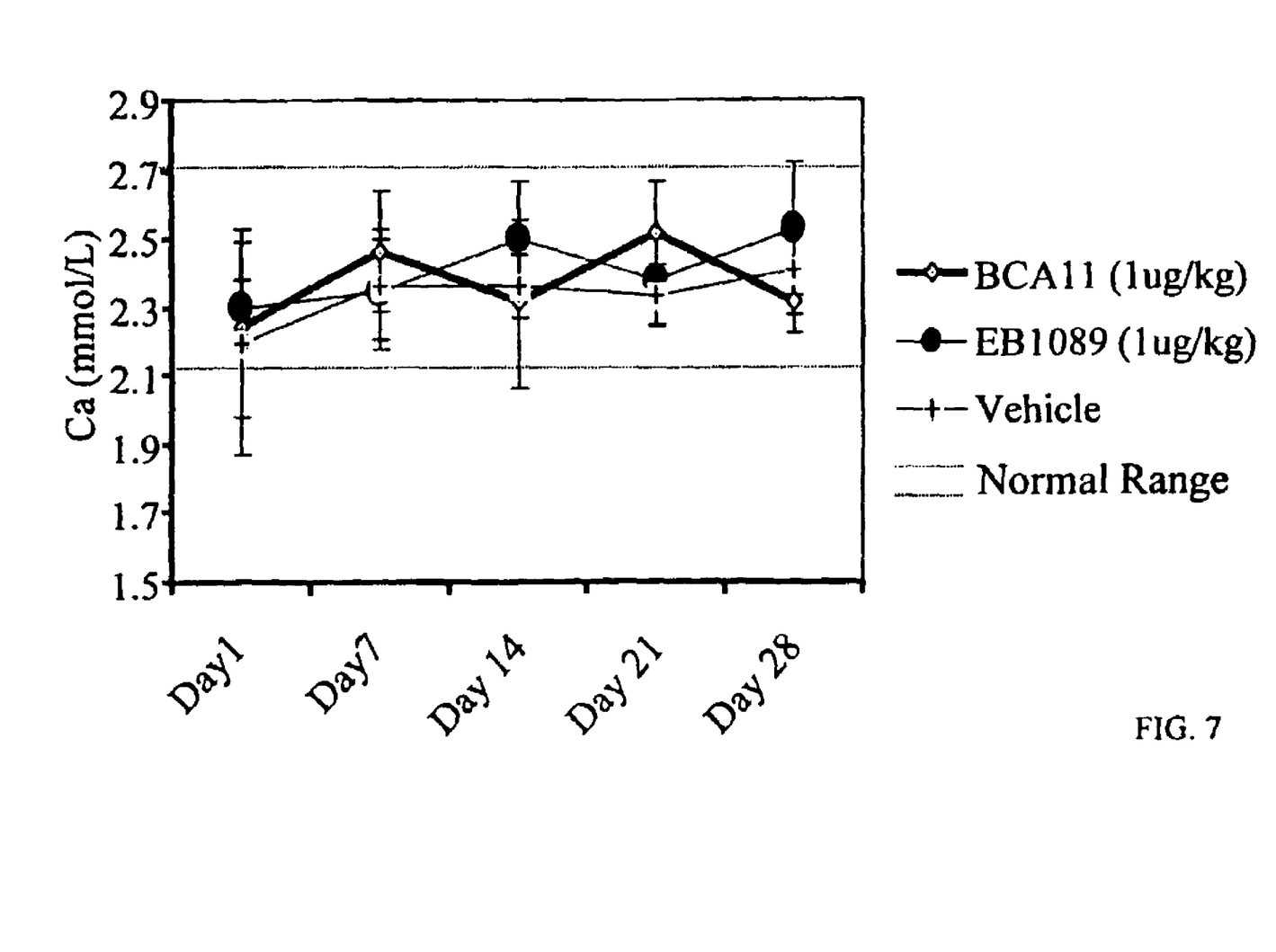
FIG. 7 is a line graph of calcium (Ca) (mmol/L) vs. day of treatment, which shows that chronic administration of BCA11 (1 μg/kg) compared with a vitamin D analog, EB1089 (1 μg/kg) or vehicle control, does not increase serum calcium levels above the normal range.

MCF-7 cells were injected with Matrigel (10 mg/ml) into 7 weeks old female athymic nude mice. Tumors were grown in the presence of implanted estrogen pellets (0.72 mg pellets). After four weeks inoculation, mice were treated for 5 weeks with hormones or vehicle (propylene glycol) control on alternate days. BCA11 and EB1089 were added at a concentration of 1 µg/kg. Serum was drawn throughout hormone treatment from the orbital vein of the mice and assayed by the Department of Clinic Chemistry, National Institutes of Health, by methods well-known in the art. FIG. 7 shows that calcium levels (mmol/L) for either BCA11- or EB 1089-treated animals fell within the normal range of physiological calcium. Similar results were obtained from multiple blood samples taken from the phase II study. Calcium and phosphorous levels were assayed by Ani Lytics and fell within normal ranges. In addition, alkaline phosphatase, albumin, bilirubin and creatinine levels were measured in both phases. Further, VDR antagonists, BCA11 and BCA21, inhibit selectively the growth stimulatory effects of calcitriol without causing hyper- or hypo-calcemia. Additionally, histological analysis showed no abnormalities, and serum calcium, phosphorus, liver and renal functions were within the normal range, indicating that the compounds of the invention have low toxicity. These results demonstrate that a selective VDR antagonist can be used to treat breast cancer, such as estrogen-resistant breast cancer.

Example 7

Effect of Vitamin D on Tumor Growth

BT20 cells (estrogen receptor-negative, human breast cancer cells; 5 million) were injected with Matrigel (10 mg/ml) into each flank of 10 weeks old female athymic nude mice. Tumor growth was monitored for six weeks on a low-calcium diet (0.4% Ca, 0.3% P and no vitamin D; Harlan Teklad). Then, mice bearing equal number and size tumors were randomly selected for treatment groups. One group continued on the low-calcium diet (serum 25-OH-$D_3$ approx. 2 pg/ml) and received vehicle and the other group was placed on a normal diet (1.19% Ca, 0.86% P, and 6.6 mg/kg vitamin D; serum 25-OH-$D_3$ approx. 18 pg/ml) and received vehicle. Tumor volume (mm 3) was higher in the group receiving vitamin D (approx. 37 $mm^3$ at 41 days after inoculation) than in the group that did not receive vitamin D (approx. 18 $mm^3$ at 41 days after inoculation). These data indicate that tumor growth increases in the presence of vitamin D.

Six weeks old female athymic mice were placed on diets of 0.5% Ca, 0.3% P, and either no vitamin D (serum 25-OH-$D_3$ approx. 3 pg/ml; serum calcitriol approx. 30 pg/ml) or vitamin D (4 mg/kg (serum 25-OH-$D_3$ approx. 34 pg/ml; serum calcitriol approx. 370 pg/ml) or 40 mg/kg (serum 25-OH-$D_3$ approx. 73 pg/ml; serum calcitriol approx. 70 pg/ml)). Two weeks later, BT20 cells (5 million) were injected with Matrigel (10 mg/ml) into each flank and tumor growth was monitored in the absence of drug treatment. Thirty-six days after injection of BT20 cells, tumor volume was approximately 15.5 $mm^3$ in the group receiving no vitamin D, approximately 12.5 $mm^3$ in the group receiving 4 mg/kg vitamin D, and approximately 9.5 $mm^3$ in the group receiving 40 mg/kg vitamin D. At day 18, the number of tumors per injection site was highest in the group that did not receive vitamin D, followed by the group that received 4 mg/kg vitamin D and then the group that received 40 mg/kg vitamin D. At day 69, tumor weight in mice that did not receive vitamin D was approximately 0.2 g, whereas tumor weight in mice receiving 4 mg/kg vitamin D was approximately 0.3 g and tumor weight in mice receiving 40 mg/kg vitamin D was approximately 0.19 g.

Example 8

VDR Antagonists Inhibit Growth of Estrogen Receptor-Negative Breast Cancer in Vivo BT20 cells (estrogen receptor-negative, human breast cancer cells; 5 million) were injected with Matrigel (10 mg/ml) into each flank of 10 weeks old female athymic nude mice. Mice were maintained on a low-calcium diet (0.4% Ca, 0.3% P and no vitamin D; Harlan Teklad). Then, mice bearing equal number and size tumors were randomly selected for treatment groups. One group continued on the low-calcium diet (serum 25-OH-D$_3$ approx. 2 pg/ml) and the other group was placed on a normal diet (1.19% Ca, 0.86% P, and 6.6 mg/kg vitamin D; serum 25-OH-D$_3$ approx. 18 pg/ml). Treatment groups received 1.5 µg/kg BCA11 at approximately 21 days after injection of cells. Control groups received vehicle (25% propylene glycol and 75% saline). Drugs or vehicle were injected i.p. three times per week. Tumor growth was monitored biweekly with caliper measurements. Tumor volumes were calculated using the formula $\frac{1}{6}\pi\{\text{diameter}_1 \times \text{diameter}_2\}^{3/2}$ as reported by Colston et al. (Biochem. Pharmacol. (1992)). At 56 days after injection of cells (35 days after start of treatment), the tumor volume in mice receiving vehicle was approximately 49 mm$^3$, wheras the tumor volume in mice receiving BCA11 was approximately 12 mm$^3$.

Six weeks old female athymic mice were placed on diets of 0.5% Ca, 0.3% P, and vitamin D (4 mg/kg; serum 25-OH-D$_3$ approx. 34 pg/ml; serum calcitriol approx. 370 pg/ml). Two weeks later, BT20 cells (5 million) were injected with Matrigel (10 mg/ml) into each flank and tumor growth was monitored in the absence of drug treatment. After about four weeks, the mice were divided into treatment and control groups. Treatment groups received either 0.5 µg/kg BCA11 (VDR antagonist) or 1.0 g/kg EB1089 (VDR agonist). Control groups received vehicle (25% propylene glycol and 75% saline). Drugs or vehicle were injected i.p. three times per week. Tumor growth was monitored biweekly with caliper measurements. Tumor volumes were calculated as indicated in Example 7. After around 60 days of treatment, the tumor volume in mice receiving vehicle was approximately 24 mm$^3$, whereas the tumor volume in mice receiving EB1089 was approximately 14 mm$^3$ and the tumor volume in mice receiving BCA11 was approximately 8 mm$^3$. At day 69, tumor weight was approximately 0.29 g for control groups, 0.09 g for groups treated with 0.5 µg/kg BCA11, and 0.07 for groups treated with 1.0 µg/kg EB1089. Administration of 1.5 µg/kg BCA11 resulted in a tumor weight of approximately 0.12 g at 69 days, whereas administration of 3 µg/kg BCA31 resulted in a tumor weight of approximately 0.17 g, and co-administration of 1 µg/kg EB1089 and 1 µg/kg BCA31 resulted in a tumor weight of approximately 0.80 g.

BCA11(0.01 nM-100 nM), in combination with 1 nM calcitriol, also has been found to inhibit calcitriol-insensitive cancers, such as human prostate cancer (DU145 cells) and human osteosarcoma (Saos-2 cells)

Example 9

Synthesis of BCA21 and BCA31

Forty µL of 1.0 M 1,3-dicyclohexylcarbodiimide were added to the solution of 1.0 mg (2.55 µmol) of 4,4-difluoro-5-(4-phenyl-1,3-butadienyl)-4-bora-3a,4a-diaza-s-indacene-3-propionic acid, 1.0 mg (2.5 µmol) 1,25-hydroxycholecalciferol, and 1.0 mg (8.185 µmol) 4-dimethylaminopyridine in 500 mL dichloromethane. The reaction mixture was stirred in the dark and at room temperature under argon for 6 hours. Fifty µL of 1,3-dicyclohexylcarbodiimide were added at 2.75 hrs and at 4.25 hrs. Another 0.5 mg (1.27 mg) of 4,4-difluoro-5-(4-phenyl-1,3-butadienyl)-4-bora-3a,4a-diaza-s-indacene-3-propionic acid was added at 3.5 hrs. Gravity column chromatography (11 cm×1 cm, preparative C18 125 Å Bulk Packing Material [Waters Corporation], eluting with 100% acetonitrile) was used to separate the crude residue to produce 10 mg of the 1α-BODIPY ester and the 1α,3β bisubstituted BODIPY ester of 1,25-hydroxycholecalicefierol. Compounds were then further purified using HPLC with a reverse phase silica column.

All references, including publications, patent applications, and patents, cited herein, as well as U.S. provisional patent application Nos. 60/300,409 and 60/299,570, are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A compound of formula:

wherein X is a $C_{2-10}$ spacer, and R is a substituted or an unsubstituted $C_{6-30}$ aryl, an unsubstituted $C_{5-30}$ heteroaryl, where R' and R" are independently a substituted or unsubstituted aryl or a substituted or unsubstituted alkyl, or a moiety selected from the group consisting of wherein said compound is a vitamin D receptor (VDR) antagonist.

2. A compound of formula wherein X is CH$_2$CH$_2$ and R is:

3. A compound of formula wherein X is CH$_2$CH$_2$ and R is:

4. A compound of formula wherein X is (CH$_2$)$_{10}$ and R is:

5. A compound of formula wherein X is CH₂CH₂ and R is:

6. A compound of formula wherein X is CH₂CH₂ and R is:

7. A composition comprising the compound of any one of claims 1-6 and a carrier.

8. The composition of claim 7, wherein the composition is a pharmaceutical composition and the carrier is a pharmaceutically acceptable carrier.

9. A method of treating a patient for a disease that can be treated therapeutically by administration of a VDR antagonist, which method comprises administering an effective amount of the composition of claim 7 to a patient in need thereof, wherein the disease is breast cancer.

* * * * *